United States Patent [19]

Milovidov et al.

[11] Patent Number: 4,565,788

[45] Date of Patent: Jan. 21, 1986

[54] METHOD OF DETERMINING HEAT LOSSES DUE TO INCOMPLETE FUEL COMBUSTION

[76] Inventors: Boris A. Milovidov, ulitsa Kalinina, 143, kv. 25, Pavlodar, U.S.S.R.; Iosif B. Kaplunov, deceased, late of Moscow, U.S.S.R.; by Nadezhda V. Kaplunova, administratix, Simonovsky val, 22 korpus 2, kv. 155, Moscow, U.S.S.R.

[21] Appl. No.: 624,780

[22] Filed: Jun. 26, 1984

Related U.S. Application Data

[62] Division of Ser. No. 468,982, Feb. 23, 1983, Pat. No. 4,481,168.

[51] Int. Cl.[4] .................... G01N 31/12; G01N 25/22; G01N 25/00
[52] U.S. Cl. ..................... 436/137; 73/112; 374/37; 374/38; 431/12; 431/76; 436/143; 436/155; 436/158; 436/160
[58] Field of Search ................. 436/50, 136, 137, 143, 436/155, 157, 158, 160; 374/31, 36, 37, 38; 73/112; 431/12, 76

[56] References Cited

U.S. PATENT DOCUMENTS

| | | | |
|---|---|---|---|
| 3,324,715 | 6/1967 | Held | 73/112 |
| 4,423,487 | 12/1983 | Buckenham et al. | 73/112 X |
| 4,433,922 | 2/1984 | Bohl et al. | 374/36 |

FOREIGN PATENT DOCUMENTS

| | | | |
|---|---|---|---|
| 2832862 | 2/1980 | Fed. Rep. of Germany | 422/78 |
| 0937248 | 9/1963 | United Kingdom | 374/36 |
| 2016707 | 9/1979 | United Kingdom | 431/76 |
| 1562536 | 3/1980 | United Kingdom | 431/76 |
| 2081856 | 2/1982 | United Kingdom | 431/12 |
| 0375449 | 5/1973 | U.S.S.R. | |
| 0391355 | 12/1973 | U.S.S.R. | |
| 0402790 | 3/1974 | U.S.S.R. | |
| 0821845 | 4/1981 | U.S.S.R. | 431/76 |

OTHER PUBLICATIONS

Popov et al., "Power Stations" Journal, No. 1, (1973), Apparatus for Determining Heat Losses Due to Mechanical Underburning.

Primary Examiner—Arnold Turk
Assistant Examiner—Robert J. Hill, Jr.
Attorney, Agent, or Firm—Steinberg & Raskin

[57] ABSTRACT

A method of determining heat losses due to incomplete fuel combustion consists in that periodic sampling of fuel combustion products is carried out. The sample is separated into two parts, one of which includes a gaseous phase, and the other, solid and gaseous phases. Oxygen concentration in each part is assessed, after which both parts are heated and burnt up to determine oxygen concentration after burning. Oxygen losses in the gaseous phase and in the mixture of the solid and the gaseous phases are determined, and heat losses due to chemical and total underburning of fuel are defined as the ratio between oxygen losses. Then heat losses due to mechanical underburning of fuel are estimated as the difference of heat losses due to total chemical and mechanical underburning, and chemical underburning of fuel. There is also disclosed a device for determining heat losses due to incomplete fuel combustion, comprising two chambers with electric heaters for finish burning of the sample, interconnected by a separation valve. One of the chambers contains a partition, made from a porous material, to retain the solid phase of the sample in the chamber. The device is provided with means for suction and discharge of the sample, and means for measuring the thermal effect of the sample combustion reaction.

1 Claim, 2 Drawing Figures

METHOD OF DETERMINING HEAT LOSSES DUE TO INCOMPLETE FUEL COMBUSTION

This is a divisional application of co-pending U.S. Patent App. Ser. No. 468,982, filed Feb. 23, 1983, now U.S. Pat. No. 4,481,168.

BACKGROUND OF THE INVENTION

The present invention relates to means of monitoring and control of fuel combustion processes and, more precisely, to a method of determining heat losses due to incomplete fuel combustion and a device for implementing the same.

The invention is intended for use in systems of monitoring and control of fuel combustion processes at thermal power stations, in boiler plants and industrial furnaces, operating on solid, liquid and gaseous fuels.

The quality of fuel burning processes depends on the degree of completion of the combustion process in combustion chambers. The resultant heat losses are caused by chemical and mechanical underburning of fuel, and condition excessive consumption of the latter. The amount of these losses is dependent both on the construction of furnace and fuel burning preparation systems, and on the specifics of operation thereof. Control over the running values of these losses makes it possible to timely influence the operating conditions: supply of oxidizer (air), its temperature, and the degree of fuel comminution. Maintaining optimal values of these parameters allows heat losses due to incomplete fuel combustion and, consequently, excessive fuel consumption and discharge of unburnt fuel into the atmosphere to be reduced to a minimum. At the present time the problem of control over heat losses due to incomplete fuel combustion has not yet been fully solved. This is particularly true of operation on solid fuel, entailing considerable losses of heat due to both mechanical and chemical underburning. Control over mechanical underburning presents the most severe problem.

The value of heat losses caused by mechanical or chemical underburning is expressed in per cent of the amount of heat released in the event of complete fuel combustion and is calculated by relevant formulas, including calorific value of fuel, composition of combustible components remaining after burning thereof, heat of combustion, fuel ash content, and amount of ash in the fly ash and slag. These values vary considerably even within the same lot of fuel.

Monitoring of heat losses due to incomplete fuel combustion is generally carried out by analyzing the composition and the number of combustible components, the results of the analysis providing the basis for appraising the quality of the fuel combustion process. However, variability of values making part of the design formula is conducive the appreciable errors in determining heat losses due to incomplete fuel combustion, which does not alow the fuel combustion process to be optimized even in case of a very accurate analysis of combustible components in the remaining unburnt fuel.

One prior art method of determining chemical underburning of a liquid or a gaseous fuel (cf. USSR Inventor's Certificate No. 402,790, cl. F23 N 5/14) consists in that a sample of flue gases is separated into two parallel flows, with a dose of oxygen being injected in one of them, and a predetermined amount of a combustible component, in the other. The mixture is finish-burnt in each flow, and assessment is made of the amount of heat liberated thereat in each flow. The amount of combustibles in the sample is judged by the amount of heat released in the first flow, and the amount of oxygen contained in the sample is estimated on the basis of the amount of heat released in the second flow.

Separating the sample into two flows and introducing additional reagents complicates the method and conditions the dependence of the results of measurements on the precision of reagent metering, and omission of the running value of the fuel calorific power affects the accuracy in determining heat losses. Furthermore, heat loss estimation necessitates additional calculations. The method is not applicable to determining heat losses due to mechanical underburning.

Another prior art method of determining the content of combustibles in the fly ash (cf. USSR Inventor's Certificate No. 391,355, cl. F23 B 5/24) consists in that a sample of ash is passed between capacitor plates to measure the variation of its capacitance depending on carbon content in the sample.

Variation of carbon concentration gives rise to a change in the value of permittivity of the medium in the electric field of the capacitor. The results of measurements are largely influenced by the presence of other components making up the sample, and also by extraneous impurities. This circumstance causes insufficient accuracy of measuring the content of combustibles in the sample and the total error in determining heat losses due to incomplete fuel combustion.

Known in the art is a device for determining the content of combustibles in fly ash (cf. USSR Inventor's Certificate No. 375,449, cl. F23 N 5/24), comprising a sampler, a separator to isolate the coarse fraction of the sample, a screw feeder, a capacitor, and an indicator of carbon content in the sample.

Passsing the sample through the separator leaves particles of the fine fraction out of the sample, which does not give a clear idea of the sample composition and adds to the error in defining heat losses due to incomplete fuel combustion.

Another prior art method of determining heat losses due to incomplete fuel combustion consists in that a sample of fuel combustion products is periodically drawn, heated to the temperature of ignition of the combustible remaining in this sample to assist burning, and the quantity of heat given off after finish burning of the sample is assessed, whereby losses of heat due to incomplete fuel combustion are judged ("Power Stations" Journal, No. 1, 1973. K. N. Popov, E. V. Agafonov, L. N. Matonin. "Apparatus for Determining Heat Losses Due to Mechanical Underburning").

According to said method, the quantity of heat liberated during sample burning is determined from the change of temperature in the furnace, thereby estimating the amount of combustibles in the sample. Following this, appraisal is made of heat losses due to incomplete fuel combustion, taking into account ash content and fuel calorific value, additionally determined for calculations. The influence of errors in determining all values necessary for calculations reduces considerably the accuracy of assessing heat losses due to incomplete fuel combustion.

Also known in the art is a device for determining heat losses due to incomplete fuel combustion, comprising a chamber for finish burning of the sample, provided with an electric heater, and a means for measuring the thermal effect of the fuel combustion reaction associated with the chamber ("Power Stations" Journal, No. 1, 1973. K. N. Popov, E. V. Agafonov, L. N. Matonin. "Apparatus for Determining Heat Losses Due to Mechanical Underburning").

The chamber for finish burning of the sample incorporated in said device is made in the form of a cylinder with the axis thereof making an angle to the horizontal. The electric heater revolves around the chamber for finish burning of the sample. A sample of fuel combustion products is periodically charged into the chamber. As the chamber rotates, the sample is stirred and displaced along the axis of the chamber. The time of the sample finish burning is 10 minutes, which is sufficient for proximate laboratory analysis, but insufficient for timely interference in the process during automatic control of the fuel combustion process.

The thermal effect of the fuel combustion reaction is determined by a rise in temperature in the chamber for finish burning of the sample with the help of thermocouples installed therein. The amount of liberated heat is used to calculate the heat losses due to mechanical underburning of fuel.

Besides, fluidity of the heat flow during sample burning causes an appreciable error in measuring the temperature, whereby the content of combustibles in the sample is judged. The aforesaid does not allow precise and reliable assessment of heat losses due to incomplete fuel combustion.

SUMMARY OF THE INVENTION

An object of the present invention is to provide a method of determining heat losses due to incomplete fuel combustion and a device for implementing the same, which would make it possible to enhance accuracy and reliability in appraising heat losses due to chemical and mechanical underburning.

The foregoing object is accomplished by a method of determining heat losses due to incomplete fuel combustion, consisting in that a sample of fuel combustion products is periodically drawn, heated to the temperature of ignition of the combustible remaining in this sample to assist burning, and the quantity of heat liberated during sample burning is estimated, whereby heat losses due to incomplete fuel combustion are judged, according to the invention, wherein sampling of fuel combustion products including a solid and a gaseous phases is carried out and, prior to heating the sample, the latter is separated into two parts, one of which includes a solid and a gaseous phase and the other, only a gaseous phase, an oxygen concentration $C_1$ in each part of the sample is evaluated, after which heating and burning of each part of the sample are effected with the volume of the sample maintained at a constant level, an oxygen concentration $C_2$ in the part of the sample containing only the gaseous phase and then an oxygen concentration $C_3$ in the part of the sample containing the solid and the gaseous phases are measured, an oxygen loss $\Delta_1$ in the part of the sample containing the gaseous phase is determined as the difference of the concentrations $C_1$ and $C_2$, an oxygen loss $\Delta_2$ in the part of the sample containing the solid and the gaseous phases is found out as the difference of the concentrations $C_1$ and $C_3$, an oxygen loss $\Delta_3$ in the initial oxidizer in the event of complete fuel combustion is assessed as the difference of an initial concentration $C_0$ and the concentration $C_3$, then heat losses due to chemical underburning of fuel are estimated as the ratio between the oxygen loss $\Delta_1$ in the event of finish burning of combustible gases and the oxygen loss $\Delta_3$ in the initial oxidizer in the event of complete fuel combustion therein, heat losses due to chemical and mechanical underburning of fuel are evaluated as the ratio between the oxygen loss $\Delta_2$ and the oxygen loss $\Delta_3$, heat losses due to mechanical underburning of fuel are appraised as the difference of heat losses due to total chemical and mechanical underburning and heat losses due to chemical underburning of fuel.

The foregoing object is also attained by a device for determining heat losses due to incomplete fuel combustion comprising a chamber for finish burning of the sample with an electric heater, and a means for measuring the thermal effect of the sample combustion reaction, associated with the chamber, according to the invention, is provided with an additional chamber for finish burning of the sample, fitted with an electric heater and associated with the main chamber through a separation valve, a porous partition, arranged in the main chamber, to retain the solid phase therein, a means for suction and discharge of the sample, associated with the additional chamber for finish burning of the sample through a second separation valve, the means for measuring the thermal effect of the sample combustion reaction comprising oxygen concentration sensors and temperature sensors installed in the main and additional chambers for finish burning of the sample, a control unit located outside of the chambers, with inputs thereof connected to the oxygen concentration sensors and the temperature sensors, an oxygen loss indicating unit with an input thereof connected to the output of the control unit, indicators of heat losses due to chemical and total underburning of fuel, connected to the outputs of the oxygen loss indicating unit, whereas the output of the control unit is associated with the separation valves, with the means for suction and discharge of the sample, and with the heaters of the finish-burning chambers.

It is advantageous that the chambers for finish burning of the sample installed in a gas duct the device contains a suction valve fitted at the inlet to the main chamber for finish burning of the sample and connected to the output of the control unit.

In the proposed method of determining heat losses due to incomplete fuel combustion, measurement of oxygen concentration in the oxidizer in whose medium first fuel and then the sample are burnt and estimation of heat liberated during burning by decreasing oxygen concentration make it possible to exclude the dependence of the result on several variables and reduce the dependence of the result of heat loss estimation to only one variable, i.e. oxygen concentration, which enhances accuracy and reliability.

Separation of the sample into two parts, one of which includes a solid and a gaseous phases, and the other, only a gaseous phase, makes it possible to estimate heat losses both due to only chemical and total underburning of fuel. Limiting the volume of each part of the separated sample and burning these parts, maintaining a constant volume thereof, allows the sample metering to be simplified and accuracy additionally enhanced.

Arranging the chamber for finish burning of the sample in the gas duct makes it possible to avoid the influence of sampling lines on the quality of the sample drawn, thereby additionally enhancing the accuracy and reducing sluggishness in obtaining the results of measurements. The presence of the means for suction and discharge of the sample permits complete scavenging of the main and additional chambers, complete removal of the remainders of the preceding sample and the influence thereof on the results of the analysis. Using oxygen remaining in the gaseous phase of the sample as oxidizer offers the possibility of assessing the quantity of heat liberated at different stages of burning on the basis of only one variable, i.e. the content of oxygen in the oxidizer, thereby precluding the influence of other variables and enhancing the accuracy of measurements.

BRIEF DESCRIPTION OF DRAWINGS

The invention will now be described in more detail, by way of example, with reference to the accompanying drawings, wherein.

DETAILED DESCRIPTION OF THE PREFERRED EMBODIMENTS

Figure 1:
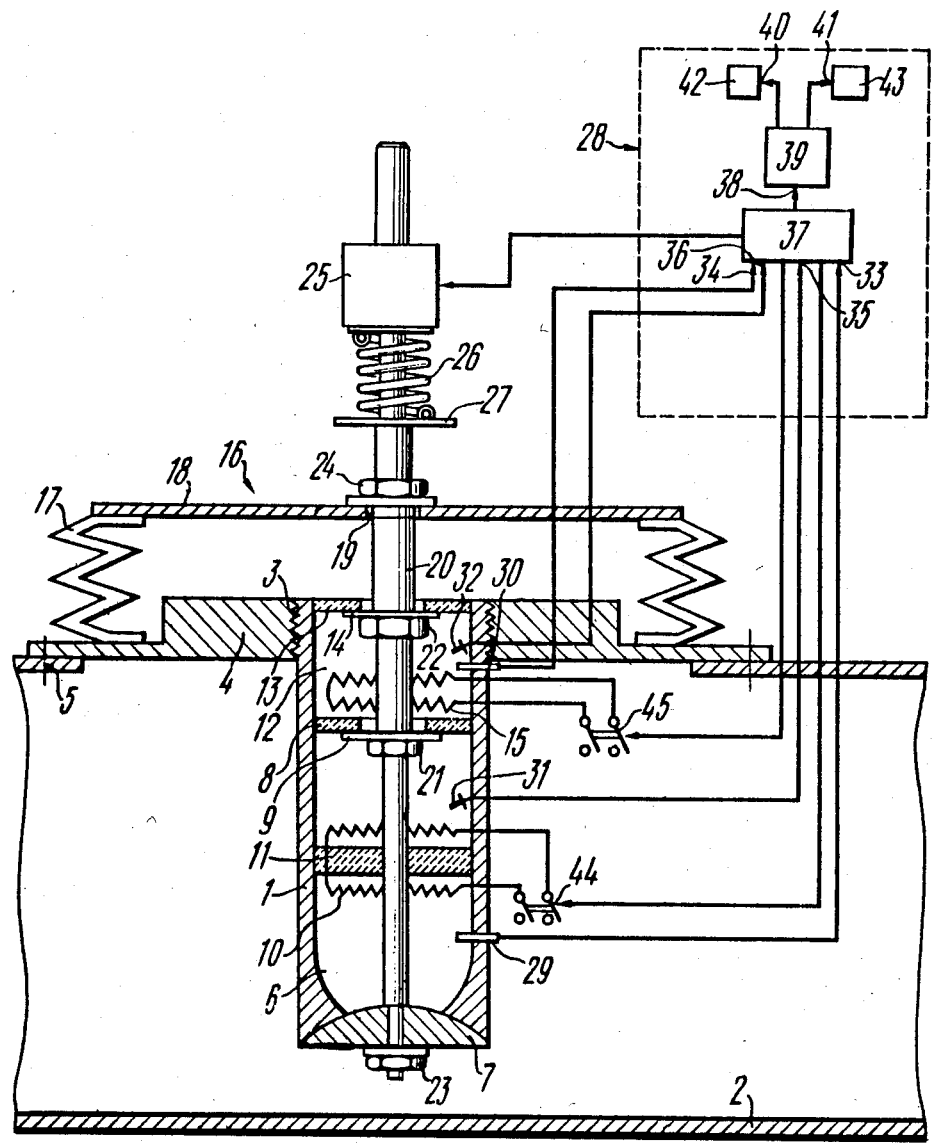
FIG. 1 illustrates a device for determining heat losses due to incomplete fuel combustion (longitudinal section through finish-burning chambers with valves closed), according to the invention.

A method of determining heat losses due to incomplete fuel combustion consists in that a sample of fuel combustion products including a solid and a gaseous phase is periodically drawn. The sample is separated into two parts, one of which includes a solid and a gaseous phases, and the other, a gaseous phase. An oxygen concentration $C_1$ in each part of the sample is measured, both parts of the sample are heated to the temperature of ignition of the combustible remaining in said sample to assist burning, the burning being effected with the volume of the sample maintained at a constant level. An oxygen concentration $C_2$ in the part of the sample containing only the gaseous phase and an oxygen concentration $C_3$ in the part of the sample containing the solid and the gaseous phases are evaluated.

Then an oxygen loss $\Delta_1$ in the part of the sample containing the gaseous phase is defined as the difference of the concentrations $C_1$ and $C_2$, an oxygen loss $\Delta_2$ in the part of the sample containing the solid and the gaseous phases is assessed as the difference of the concentrations $C_1$ and $C_3$, an oxygen loss $\Delta_3$ in the initial oxidizer in the event of complete fuel combustion is estimated as the difference of an initial concentration $C_0$ and the concentration $C_3$.

Heat losses due to chemical underburning of fuel conditioned by incomplete burning of the resultant combustible gases are appraised as the ratio between the oxygen loss $\Delta_1$ after finish burning of combustible gases of the sample and the oxygen loss $\Delta_3$ in the initial oxidizer in the event of complete fuel combustion therein, heat losses due to chemical and mechanical underburning of fuel are determined as the ratio between the oxygen loss $\Delta_2$ and the oxygen loss $\Delta_3$, and heat losses due to mechanical underburning of fuel caused by escape of unburnt solid particles of fuel are evaluated as the difference of heat losses due to total chemical and mechanical, and to chemical underburning of fuel.

A device for determining heat losses due to incomplete fuel combustion comprises a body 1 (FIG. 1) installed in a gas duct 2. A threaded connection 3 secures the body 1 on a flange 4 mounted on the gas duct 2 by means of a threaded connection.

The body 1 houses a chamber 6 for finish burning of the sample, formed by the walls of the body 1, a suction valve 7 and a partition 8 with a separation valve 9. The chamber 6 contains an electric heater 10 and a partition 11 made from a refractory porous material.

The body 1 also houses an additional chamber 12 for finish burning of the sample, intended for finish burning of only the gaseous phase of the sample. The chamber 12 is formed by the walls of the body 1, the partition 8 with the separation valve 9 and a partition 13 with a separation valve 14. The chamber 12 contains an electric heater 15.

The device also comprises a means 16 for suction and discharge of the sample, associated with the additional chamber 12 through the separation valve 14. The means 16 is made in the form of a bellows 17 with one end thereof secured on the flange 4, and the other, on a cover 18. The cover 18 has a hole 19 to pass a rod 20. The separation valves 9 and 14 and the suction valve 7 are rigidly secured on the rod 20 with the aid of nuts 21, 22 and 23. The cover 18 is attached to the rod 20 through a nut 24. The rod 20 carrries an electromagnet 25 and a spring 26, the latter bearing up against a washer 27.

The device also comprises a means 28 for measuring the thermal effect of the sample combustion reaction. The means 28 is in turn provided with sensors 29, 30 of oxygen concentration in the main and the additional chambers 6, 12 for finish burning of the sample and with sensors 31, 32 for measuring temperature in the chambers for finish burning of the sample, whose outputs are connected to inputs 33, 34, 35, 36 of a control unit 37. The output of the control unit 37 is connected to an input 38 of an oxygen loss indicating unit 39. The outputs of the unit 39 are connected to inputs 40, 41 of indicators 42, 43 of heat losses due to chemical and total underburning of fuel, respectively. The outputs of the control unit 37 are connected to the electromagnet 25 of the means 16 for suction and discharge of the sample and to switches 44, 45 of the electric heaters 11, 15 of the finishburning chambers. The control unit 37 is associated with the valves 7, 9, 14 through the rod 20 displacing under the action of the electromagnet 25.

The oxygen loss indicating unit 39 is made in the form of a computing device for storing oxygen concentration signals, computation of differences therebetween, and for division (Heat Engineering Reference Book, vol. 2, Energia Publishers, Moscow, 1980).

Figure 2:
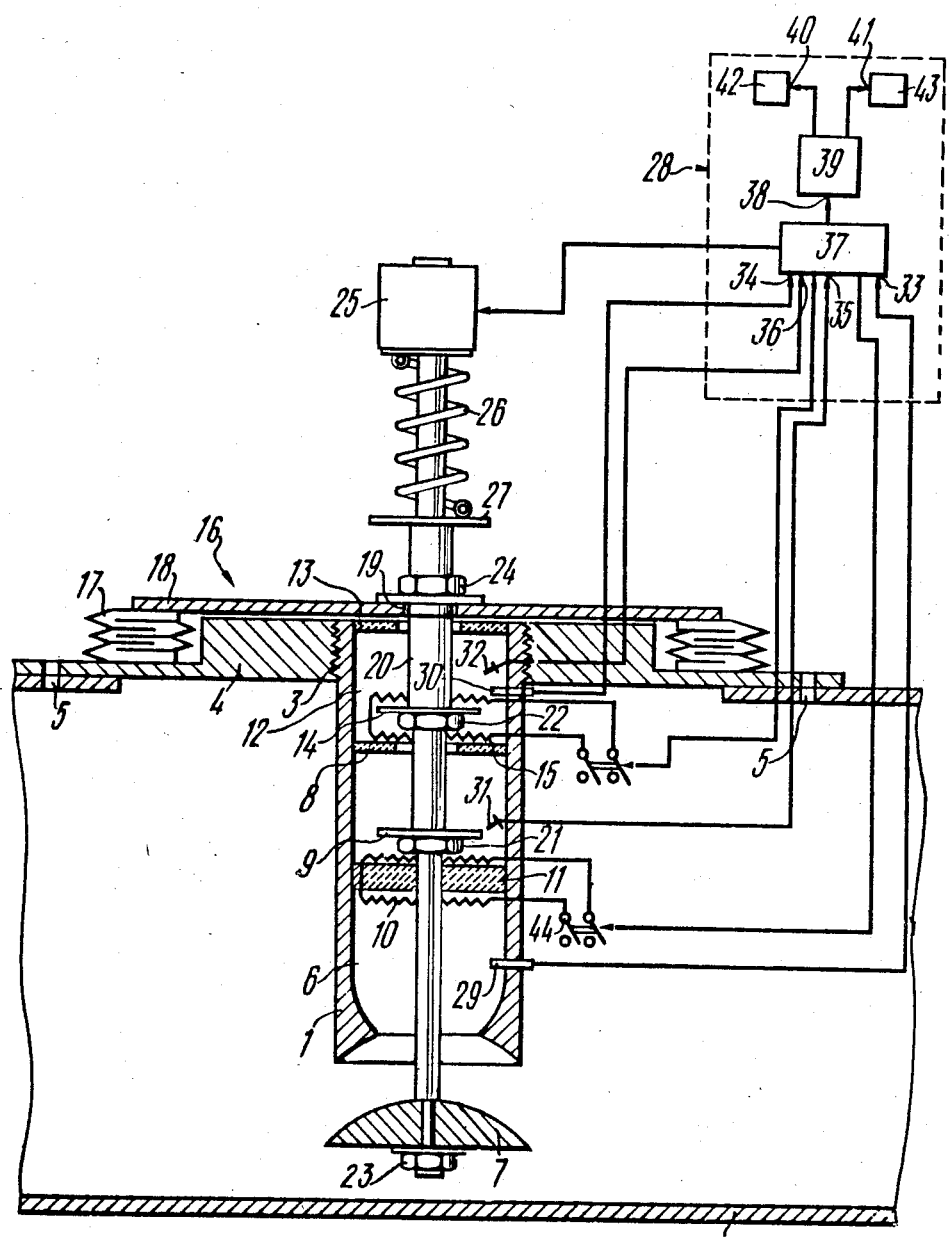
FIG. 2 shows the same as in FIG. 1 (longitudinal view with valves open), according to the invention.

FIG. 1 illustrates the device with the valves 7, 9, 14 closed, and FIG. 2 shows the device with the valves 7, 9, 14 open.

The volume of the main chamber 6 is such that the volume of the sample contains the amount of oxygen sufficient for complete burning of the combustible remaining in the solid and the gaseous phases.

The device for determining heat losses due to incomplete fuel combustion operates as follows.

In the proposed method heat losses due to chemical and total underburning of fuel are determined as the ratio between oxygen losses, heat losses $q_1$ due to chemical underburning being found from the expression:

$$q_1 = (C_1 - C_2)/(C_0 - C_3) = (\Delta_1/\Delta_3),$$

and heat losses $q_2$ due to total chemical and mechanical underburning, from the expression:

$$q_2 = (C_1 - C_3)/(C_0 - C_3) = (\Delta_2/\Delta_3).$$

In response to a signal from the control unit 37 (FIGS. 1, 2) the electromagnet 25 operates, thereby causing the rod 20 to displace downwardly and the valves 7, 9, 14 to open. The chambers 6, 12 are evacuated and scavenged. Following this, a signal from the control unit 37 turns off the electromagnet 25, returning the rod 20 to the initial position and closing the valves 7, 9, 14. As this takes place, a sample is drawn in from the gas duct 2. In the beginning the sample comes to the chamber 6. Solid fuel particles (solid phase) settle on the porous partition 11 of the chamber 6, whereas the purified gaseous phase partially flows into the chamber 12 for finish burning of the sample.

The volume of the buffer vessel in the bellows 17 is somewhat larger than the total volume of the chambers 6, 12 for finish burning of the sample. The volume of the additional chamber 12 does not affect the valve $q_1$ and, for that matter, the accuracy of measuring heat losses due to chemical underburning of fuel. It is practicable, therefore, to restrict its volume to a minimum, proceeding only from design considerations regarding the arrangement of the electric heater 15 and the sensors 30, 32.

An increase in the concentration of the solid phase relative to the average concentration in the sample takes place within the main chamber 6. This increase can be defined as the ratio between the volume of the main chamber and the total volume of the sample, said ratio predetermining a proportionality coefficient $K_1$ in the denominator of the formula for assessing heat losses due to chemical and total underburning of fuel, and also a proportionality coefficient $K_2$ in the numerator of the formula for evaluating heat losses due to chemical underburning of fuel.

Accordingly, heat losses $q_1$ and $q_2$ are found from the expressions:

$$q_1 = (1/K_1)(\Delta_1/\Delta_3);$$

$$q_2 = (K_2/K_1)(\Delta_2/\Delta_3)$$

When burning fuel with only an insignificant excess air, the amount of oxygen in the sample may prove insufficient for burning of the remaining combustible. In such cases it is advantageous to install the device in the gas duct in the immediate proximity of likely places of atmospheric air inflow or to mix the sample with atmospheric air prior to injecting it into the chambers 6, 12.

After the valves 7, 9, 14 have closed, the oxygen concentration $C_1$ prior to finish burning is estimated in both parts of the sample. Then the electric heaters 11, 15 are energized to raise the temperature in the chambers 6, 12 up to the temperature of ignition of the combustible remaining in the sample. Combustibles in both parts of the sample burn up, with the volume of the main and additional chambers 6, 12 maintained at a constant level.

After the sample has burnt up, the oxygen concentration sensors 29, 30 are switched on, the signal wherefrom arrives at the oxygen loss indicating unit 11. The electric heaters 11, 15 and the sensors 29, 30 are then deenergized, the electromagnet 25 operates, and the operating cycle is repeated.

During analysis of the sample the oxygen loss indicating unit 11 registers oxygen concentration signals coming from the sensors 29, 30. The signal of the initial concentration $C_0$ of oxygen in the oxidizer is introduced as a constant. On the basis of these signals the operation of appraising the oxygen losses $\Delta_1$, $\Delta_2$, $\Delta_3$ and the operation of dividing the same with the coefficients $K_1$ and $K_2$ duly taken into account are performed. The results of division are registered by the indicators 42, 43 graduated in per cent of the available heat.

What is claimed is:

1. A method of determining heat losses due to incomplete fuel combustion, which comprises:

periodically taking a sample of fuel combustion products, said sample including solid and gaseous phases;

separating the sample into two parts, one of which includes a solid and a gaseous phase; and the other, a gaseous phase;

determinng an oxygen concentration $C_1$ in each of said parts of said sample;

heating said parts of said sample to the temperature of ignition of combustible material remaining in said parts to assist burning, while maintaining the volume of said parts at a constant level;

determining an oxygen concentration $C_2$ after said heating in the part of the sample containing only said gaseous phase;

determining an oxygen concentration $C_3$ after said heating in the part of the sample containing said solid and said gaseous phases;

determining an oxygen loss $\Delta_1$ in the part of said sample containing said gaseous phase as the difference of said concentrations $C_1$ and $C_2$;

determining an oxygen loss $\Delta_2$ in the part of said sample containing said solid and said gaseous phases as the difference of said concentrations $C_1$ and $C_3$;

determining an oxygen loss $\Delta_3$ in an initial oxidizer in the event of complete combustion of fuel as the difference of an initial oxygen concentration $C_0$ and said concentration $C_3$;

determining heat losses due to chemical underburning of fuel as the ratio between said oxygen loss $\Delta_1$ and said oxygen loss $\Delta_3$, multiplied by a first coefficient predetermined from the ratio of the volume of the part of the sample having the gas/solid phases and total volume of the sample;

determining heat losses due to chemical and mechanical underburning of fuel as the ratio between the oxygen loss $\Delta_2$ and the oxygen loss $\Delta_3$, multiplied by a second coefficient predetermined from the ratio of the volume of the part of the sample having the gas/solid phases and total volume of the sample; and determining heat losses due to mechanical underburning of the fuel as the difference of said heat losses due to said chemical and said mechanical underburning of fuel, and said heat losses due to said chemical underburning of fuel.

* * * * *